United States Patent
Ye et al.

(10) Patent No.: US 8,878,926 B2
(45) Date of Patent: Nov. 4, 2014

(54) APPARATUS AND METHOD FOR ANALYZING THERMAL PROPERTIES OF COMPOSITE STRUCTURES

(75) Inventors: Zheng John Ye, Santa Clara, CA (US); Kartik Ramaswamy, San Jose, CA (US); Troy S. Detrick, Los Altos, CA (US); Kenneth S. Collins, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 290 days.

(21) Appl. No.: 13/236,039

(22) Filed: Sep. 19, 2011

(65) Prior Publication Data

US 2012/0069174 A1 Mar. 22, 2012

Related U.S. Application Data

(60) Provisional application No. 61/383,979, filed on Sep. 17, 2010.

(51) Int. Cl.
*G01N 25/72* (2006.01)

(52) U.S. Cl.
CPC .......... *G01N 25/72* (2013.01)
USPC .................. 348/92; 348/E07.085

(58) Field of Classification Search
CPC .......... G01N 21/8806; G06T 2207/30164; G06T 7/0004; G06T 7/001; H04N 7/183
USPC .......... 348/92
See application file for complete search history.

(56) References Cited

U.S. PATENT DOCUMENTS

| | | | | |
|---|---|---|---|---|
| 4,578,584 A | * | 3/1986 | Baumann et al. | 250/341.4 |
| 5,834,661 A | | 11/1998 | Nonaka et al. | |
| 6,560,556 B1 | * | 5/2003 | Hopkins et al. | 702/121 |
| 7,989,729 B1 | | 8/2011 | Zhao et al. | |
| 2002/0110176 A1 | * | 8/2002 | Sun et al. | 374/5 |
| 2005/0008215 A1 | * | 1/2005 | Shepard | 382/141 |
| 2005/0231916 A1 | * | 10/2005 | Bahl et al. | 361/700 |
| 2007/0103169 A1 | * | 5/2007 | Lopez Alvarez | 324/536 |

* cited by examiner

*Primary Examiner* — Dave Czekaj
*Assistant Examiner* — Nam Pham
(74) *Attorney, Agent, or Firm* — Patterson & Sheridan, LLP

(57) ABSTRACT

Embodiments of the present invention provide methods and apparatus for analyzing thermal properties of bonding materials within a composite structure. One embodiment of the present invention provides an apparatus for analyzing thermal property of a bonding material within a structure. The apparatus comprises a structure support having a supporting surface configured to support the structure, a heat source configured to direct a heat flux to the structure supported by the supporting surface of the structure support, and a camera facing the structure supported on the structure support and configured to capture thermal images of the structure supported on the structure support.

17 Claims, 8 Drawing Sheets

APPARATUS AND METHOD FOR ANALYZING THERMAL PROPERTIES OF COMPOSITE STRUCTURES

CROSS-REFERENCE TO RELATED APPLICATIONS

This application claims benefit of U.S. Provisional Patent Application Ser. No. 61/383,979, filed Sep. 17, 2010, which is herein incorporated by reference.

BACKGROUND

1. Field of the Invention

Embodiments of the present invention relates to apparatus and methods for analyzing thermal properties of composite structures. Particularly, embodiments of the present invention provide apparatus and method for performing thermal analyzing and testing thermal properties of showerheads formed by bonding of two or more part.

2. Description of the Related Art

During semiconductor processing, it is usually desirable and optimal to expose substrates to uniform processing conditions within a processing chamber. However, various factors of the processing chamber can result in non-uniformity in processing conditions, such as non-uniform temperature, and non-uniform gas distribution.

Embodiments of the present invention provide apparatus and methods for detecting non-uniformity in thermal properties of showerheads or other composite structures.

SUMMARY

Embodiments of the present invention generally provides apparatus and methods for analyzing thermal properties by directing a heat flux to a structure and analyzing the thermal response of the structure to the heat flux.

One embodiment of the present invention provides an apparatus for analyzing thermal property of a bonding material within a structure. The apparatus comprises a structure support having a supporting surface configured to support the structure, a heat source configured to direct a heat flux to the structure supported by the supporting surface of the structure support, and a camera facing the structure supported on the structure support and configured to capture thermal images of the structure supported on the structure support.

Another embodiment of the present invention provides an apparatus for analyzing thermal properties of a showerhead having a gas distribution plate bonded to a base around by a bonding material. The apparatus comprises an anti-reflective enclosure defining a working volume, a heat source disposed in the working volume, and a structure support configured to support the showerhead so that the gas distribution plate faces the heat source. The apparatus further comprises a camera positioned to capture thermal images of the gas distribution plate disposed in the working volume.

Yet another embodiment of the present invention provides a method for analyzing condition of a bonding material within a composite structure having a first component coupled to a second component by the bonding material. The method comprises positioning the composite structure on a structure support so that the first component is facing a heat source and the heat source and the second component are in opposite sides of the first component, directing a heat flux from the heat source towards the first component, and capturing a thermal image of the component after the heat flux. The method further comprises building a temperature map of the first component from the captured thermal image, and determining condition of the bonding material according to the thermal map.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
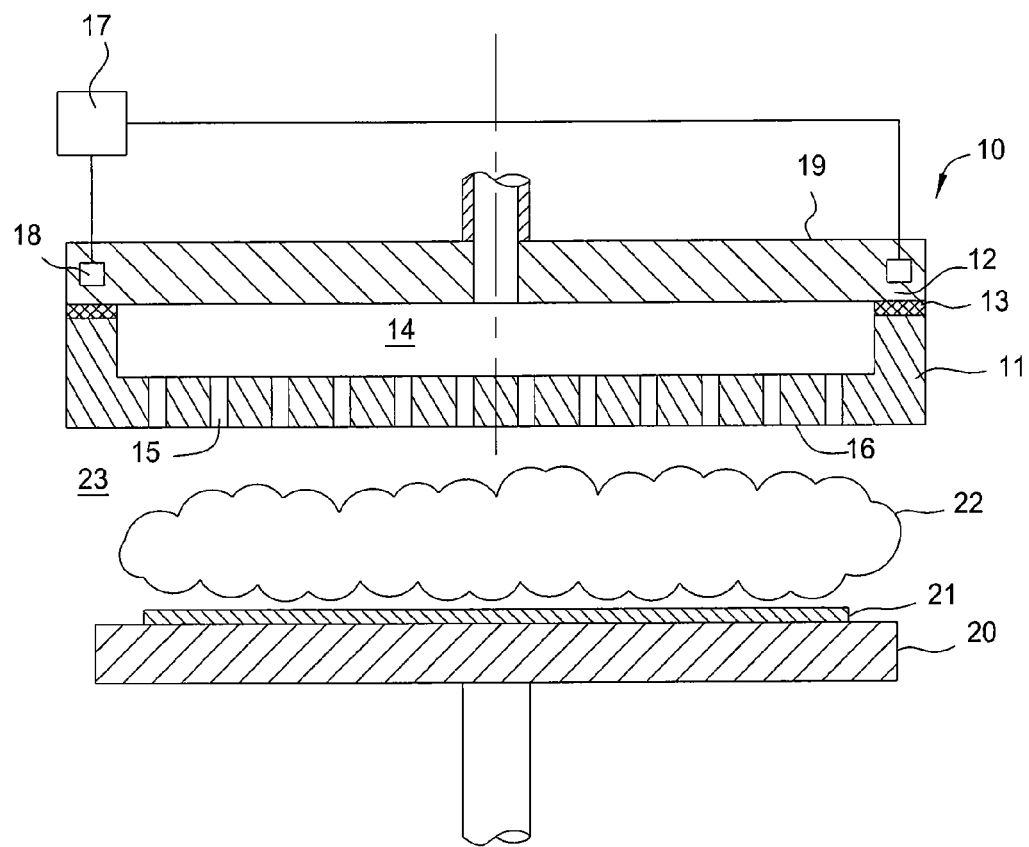
FIG. 1 is a schematic sectional side view of a composite showerhead during a plasma process.

As previously indicated, components of a processing chamber can result in non-uniformity in processing conditions, such as non-uniform temperature, and non-uniform gas distribution. Non-uniformity in processing conditions may be caused by non-uniform thermal conductivity of a showerhead. A showerhead generally includes two or more parts formed from the same or different materials due to structural and functional requirements of the showerhead. Different parts of the showerhead may be bonded together to obtain desired electrical and thermal properties. The bonding material may be non-uniformly applied or become locally separated from certain parts of the showerhead during the life of the showerhead. The non-uniform application or separation of the bonding material changes the thermal and/or electrical properties of the showerhead. As a result, the showerhead may have non-uniform thermal properties and compromise consistency and repeatability of the processes performed in the processing chamber. However, non-uniform application and other defect in the bonding material are difficult to detect from simple observation, and even more difficult to defect once the showerhead is installed in the processing chamber.

Embodiments of the present invention relates to apparatus and methods for analyzing thermal properties of composite structures. Particularly, embodiments of the present invention provide apparatus and method for analyzing thermal properties by directing a heat flux to a structure and analyzing the thermal response of the structure to the heat flux.

Embodiments of the present invention may be used to perform thermal analyzing and testing thermal properties of showerheads formed by bonding of two or more parts.

Showerheads often incorporate simultaneous heating and cooling means to maintain the desirable temperature profile with optimal process results and die yield across the substrate being processed. Due to multiple factors related to the electrical and mechanical design of a showerhead, and due to the resulting plasma conducting electrical current as well as heat load to the showerhead, the surface temperature of a showerhead often exhibits various degrees of non-uniformity of temperature distribution when subject to a heat source. While it is desirable to minimize this non-uniformity, it is usually difficult to achieve in practical sense as the requirement for uniformity usually increases with advancement in circuit design. It is often necessary to maintain the consistency of uniformity such that wafer-to-wafer variation and tool-to-tool variation may be minimized. This latter requirement of repeatability may be achieved by quality control means during equipment hardware manufacturing.

Embodiments of the present invention provides apparatus and methods for monitoring bonding materials within a composite structure. Conditions and properties of bonding material are difficult to inspect using traditional or direct methods. The conditions and properties of bonding material usually change over a lifetime of the composite structure. Embodiments of the present invention provide apparatus and methods for monitoring and maintaining consistency of thermal profile of a showerhead during lifetime of the showerhead and obtaining uniform thermal profile from one showerhead to the next. Embodiments of the present invention are particularly beneficial to inspect conditions of bonding materials that are used to glue two or more component together in a composite structure, such as a showerhead. Although the methods and apparatus are described below with reference to a composite showerhead, the composite showerhead is representative of composite structures.

FIG. 1 is a schematic sectional side view of one embodiment of a composite showerhead 10 during a plasma process. The composite showerhead 10 comprises a gas distribution plate (GDP) 11 having gas distribution holes 15 bonded to a base 12 using a thermally conductive bonding material 13. The gas distribution plate 11 and the base 12 form a cavity 14 therebetween. During processing, one or more processing gas enters the cavity 14 through the base 12 and then enters into to a processing volume 23 through the gas distribution holes 15. A plasma 22 formed from the processing gas is then ignited in the processing volume 23 to process, such as deposition or etch, a substrate 21 disposed on a substrate support 20 below the showerhead 10.

The gas distribution plate 11 and the base 12 may be formed from a material compatible with processing. The base 12 may be formed from a material different than that of the distribution plate 11. For example, the gas distribution plate 11 may be formed from silicon carbide while the base 12 may be formed from aluminum. In one embodiment, the bonding material 13 may be a chemical compound that is thermally conductive and/or an electrically isolating material. The thermal conductivity between the base 12 and the gas distribution plate 11 depends on how well the bonding material is bonded to each component and how uniformly the bonding material is applied.

The base 12 may have cooling channels 18 formed therein and connected to a cooling source 17 configured to cool the base 12. The gas distribution plate 11 may also be cooled through heat exchange with the base 12 via the bonding material 13.

During processing, heat load on the gas distribution plate 11 from the plasma 22 is dissipated to the cooled base 12 through the bonding material 13 resulting in a vertical temperature profile in the showerhead 10 as some areas of the gas distribution plate 11 may conduct heat more rapidly to the base 12 than adjacent areas of the gas distribution plate 11 resulting in a lateral non-uniformity of the showerhead temperature profile. The temperature of the showerhead 10 is at the highest on the surface of the gas distribution plate 11 in contact with the plasma 22, and gradually decreasing towards the base 12. Simultaneous lateral heat conductance also plays a role resulting surface as well as bulk temperature distribution profile of the showerhead 10. The consistency and repeatability of such profile is important to the final yield of a tool and to eventual production profitability.

Embodiments of the present invention provide apparatus and method for analyzing composite structures, such as the showerhead 10, to ensure temperature uniformity within the structure during and temperature uniformity overtime. Particularly, embodiments of the present invention provide apparatus and method for directing a heat flux towards a structure and obtaining a surface temperature map during transient thermal state or in a steady state. The surface temperature map can be then used to analyze the thermal properties of the structure. For example, identifying abnormality in the application of bonding material and/or identifying areas where the bonding material is not adherent to the adjacent showerhead components which may result in non-uniform lateral temperature profiles.

Overview

Figure 2:
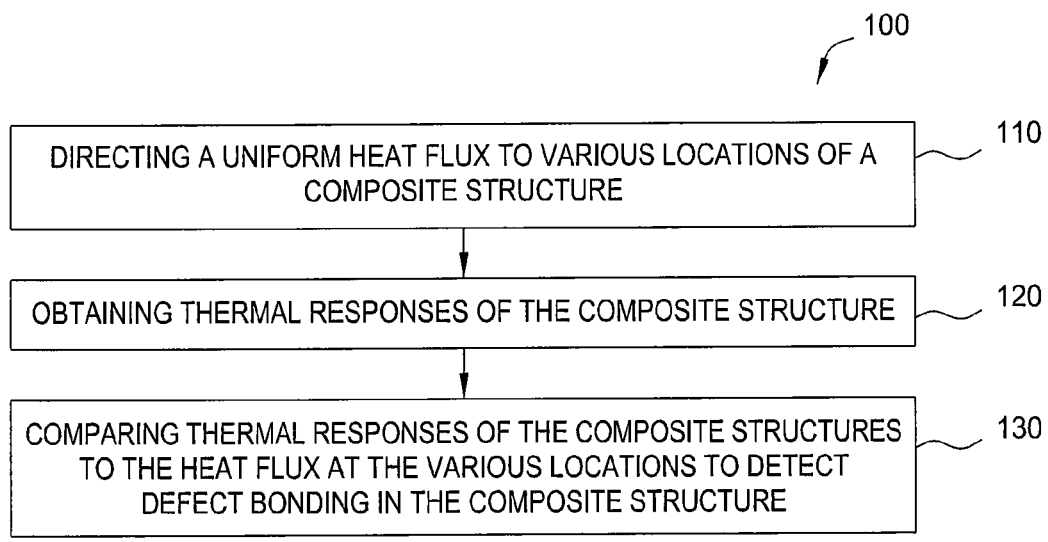
FIG. 2 is a flow diagram illustrating a method for analyzing thermal properties of composite structures in accordance with one embodiment of the present invention.

FIG. 2 is a flow diagram illustrating a method 100 for analyzing thermal properties of composite structures in accordance with one embodiment of the present invention.

In box 110, heat fluxes are directed to different portions of a composite structure so that the composite structure can react to each heat flux.

In box 120, thermal responses of the composite structure are obtained after each heat flux is delivered to the composite structure. In one embodiment, the thermal response may be utilized to obtain a lateral surface temperature profile of the composite structure after receiving the heat flux. In one embodiment, the surface temperature information may be obtained by a non-contact method, such as by taking still thermal images or video thermal images of the composite structure. In one embodiment, infrared cameras may be used to take still thermal images or video thermal images of the composite structure to obtain the lateral surface temperature profile of the composite structure. Other methods or equipment may be utilized to obtain the temperature information of the composite structure.

Figure 3:
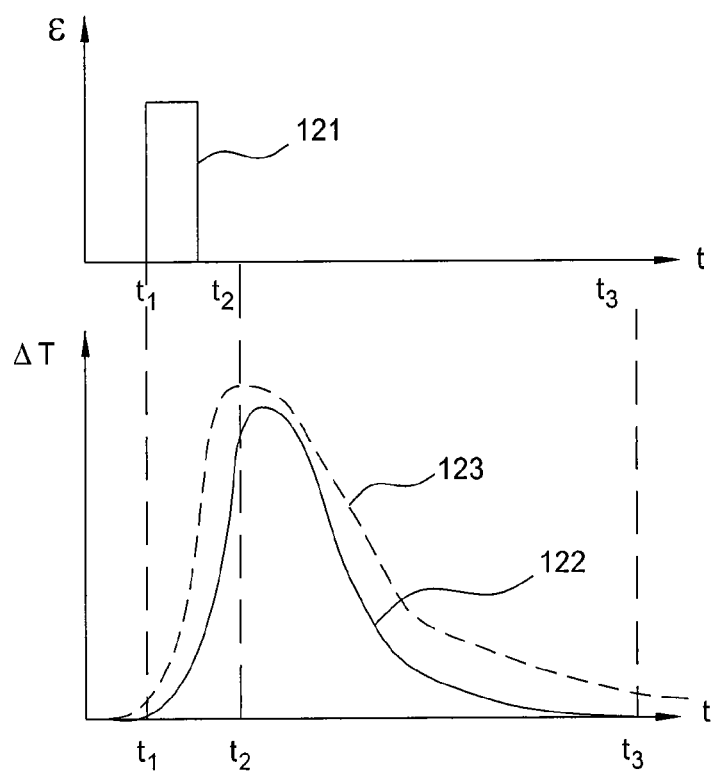
FIG. 3 illustrates schematic plots of a heat flux and responses of a composite structure to the heat flux.

FIG. 3 illustrates schematic plots of a heat flux 121 directed to a composite structure. In one embodiment, the response of the composite structure to the heat flux 121 may be characterized by analyzing local surface temperature of different regions of the showerhead 10. For example, when a heat flux is directed to a portion of the gas distribution plate 11 of the showerhead 10, the thermal energy propagates from the surface of the particular portion of the gas distribution plate 11 horizontally across the gas distribution plate 11 and vertically towards the base 12 via the bonding material. The surface temperature of the portion of the gas distribution plate 11 raises with the arrival of the heat flux 121 and decreases with the termination of the heat flux 121 and the propagation of thermal energy to the entire showerhead 10. Curve 122 schematically illustrates a typical response to the heat flux 121 in term of local temperature of the showerhead 10. When the bonding material 13 in the area wherein the heat flux 121 is directed is not in a good condition, for example becoming separated from the base 12 and/or the gas distribution plate 11, the local temperature may raise faster and decreases slower because thermal energy cannot be efficiently propagated towards the base 12 from the gas distribution plate 11. Variation in the application of the bonding material 13 in different regions of the showerhead 10 will have the same effect as separation of the bonding material, i.e. more heat transfer in areas having more bonding materials as compared to areas having less bonding materials. Curve 123 schematically illustrates the local temperature response to a heat flux when the bonding material is not in good condition.

In one embodiment, the heat fluxes directed to the different portions of the composite structure are substantially the same or uniform so that responses of the composite structure to the heat flux directed to each portion can reflect thermal properties of the particular portion of the composite structure. For example, when the composite structure is the showerhead 10, uniform heat fluxes may be directed towards different portions of the showerhead 10 at different times. Responses are obtained after each heat flux and then compared to determine the condition of bonding material 13 at different areas of the showerhead 10. As discussed above, the condition of bonding material may be the adherence of the bonding material to a component of a structure, the width or thickness uniformity of the bonding material, and variation of the longevity of the bonding material, among other bonding material property/application variation which may effect heat transfer.

Returning to FIG. 2, the thermal responses in box 120 may be a snap shot of the composite structure taken at a predetermined time after the heat flux has been applied using an infrared camera or other temperature detection device. In FIG. 3, the heat flux starts at time $t_1$, a snap shot may be taken at time $t_2$. Thus, property of the snap shot reflects the temperature of the local surface at time $t_2$ where the heat flux is directed. The delay between $t_1$ and $t_2$ allows the heat to be conducted laterally and vertically through the gas distribution plate 1. As the heat conduction is a function of the condition of the bonding material 13, variances across the gas distribution plate 11 are indicative of differences in the condition of the bonding material 13 at different areas of the gas distribution plate 11.

In another embodiment, the thermal response in box 120 may be a video of the composite structure taken during a time period after the heat flux, for example between time $t_1$ and time $t_3$. Properties of each frame of the video reflect the surface temperature of the composite structure at different times.

In box 130, the obtained thermal responses after the heat fluxes are compared or otherwise analyzed to determine the thermal uniformity of the composite structure being analyzed. For example, the variation between snap shots of curve 122 and 123 at time $t_2$ reflects a non-uniformity between the two portions of the showerhead 10 which is indicative of a difference in the bonding material 13 between these portions. When the variation of the all the responses is within a predetermined range, the composite structure, such as the showerhead 10, can be considered meeting the uniformity requirement.

In another embodiment, the obtained thermal responses may be compared with thermal responses of a standard or qualifying specimen to determine whether the composite structure being tested meets the a predetermined design criteria.

In another embodiment, the obtained thermal responses may be compared with previous thermal responses obtained from the same part to determining whether the structure being tested has deteriorated or changed overtime.

FIGS. 4A-4B, 6A-6B and 7A-7B provide exemplary embodiments for implementing the method 100.

Embodiment with Scanning Heat Source

Figure 4A:
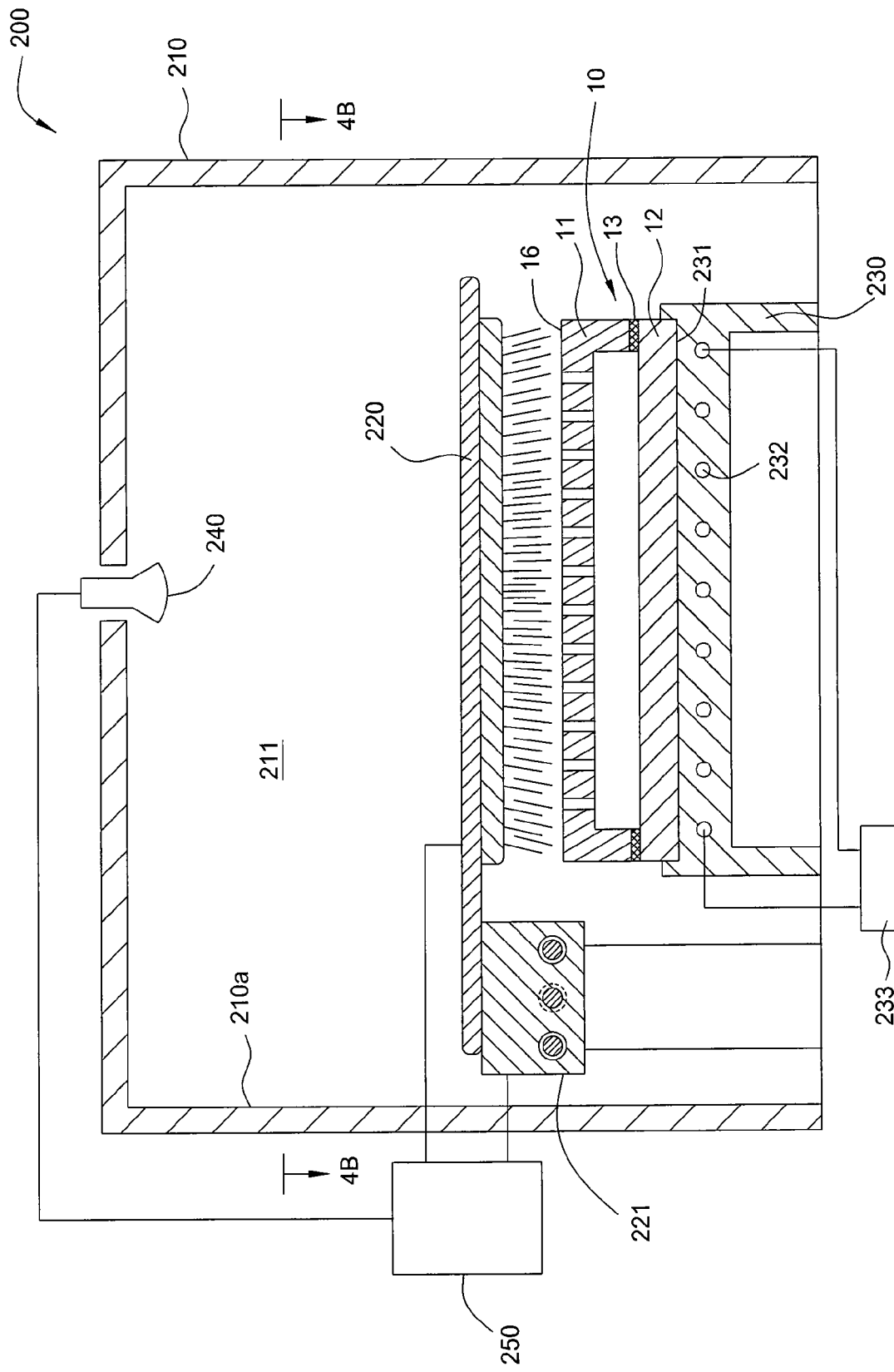
FIG. 4A is a schematic sectional side view of one embodiment of a thermal property analyzer having a linear scanning heat source.
Figure 4B:
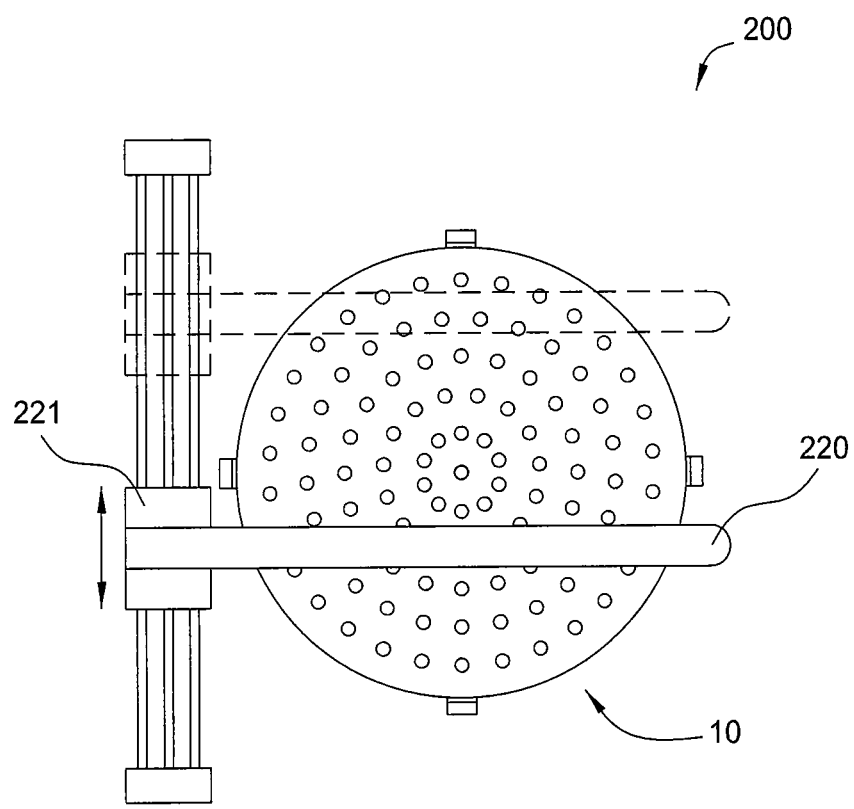
FIG. 4B is a schematic top view of the thermal property analyzer of FIG. 4A.

FIG. 4A is a schematic sectional side view of one embodiment of a thermal property analyzer 200 having a linear scanning heat source. FIG. 4B is a schematic top view of the thermal property analyzer 200 of FIG. 4A.

The thermal property analyzer 200 comprises a structure support 230 for supporting a structure being analyzed, a heat source 220 movably disposed over the structure support 230 for directing heat flux to a selected portion of the discreet structure being analyzed, and a temperature scanning device or a camera 240 disposed over the structure support 230 for obtaining temperature information such as by taking still thermal images or video thermal images of the structure that reflect thermal properties of the workpiece. The thermal property analyzer 200 further comprises an anti-reflective enclosure 210 defining a working volume 211 wherein the structure support 230, the heat source 220 and the camera 240 are disposed in the anti-reflective enclosure 210. It is contemplated that the heat source 220 may be positioned outside the enclosure 210 as long as the heat source 220 may direct heat to the structure being analyzed and the camera 240 is positioned to obtain images of the structure. The thermal property analyzer 200 further comprises a controller 250 connected to the heat source 220 and the camera 240. The controller 250 includes memory, processor, and supporting circuits.

In one embodiment, the structure support 230 is disposed in a lower portion of the working volume 211 and is configured to support a structure being analyzed, for example, the showerhead 10. The structure support 230 has a supporting surface 231 for contacting and supporting the showerhead 10 so that an outer surface 16 of the gas distribution plate 11 is maintained in a substantially horizontal orientation.

In one embodiment, the supporting surface 231 includes three or more points for contacting the showerhead 10 so that the structure support 230 has minimal thermal exchange with the showerhead 10.

In another embodiment, the structure support 230 has a plurality cooling channels 232 formed therein. The cooling channels 232 are connected to a cooling fluid source 233 configured to provide cooling fluid towards the cooling channels 232. The supporting surface 231 directly contacts an outer surface 19 of the base 12. During testing, the structure support 230 is chilled by the cooling liquid in the cooling channels 232 at a temperature lower than the temperature of the showerhead 10 and serves as a heat sink for the showerhead 10. The chilled structure support 230 accelerates dissipation of thermal energy in the showerhead 10, thus, allowing the heat source 220 to move at an increased rate during analyzing.

In one embodiment, the heat source 220 is a spot or line source with a heating area substantially smaller than the surface of the structure being analyzed. The heat source 220 is configured to provide a substantially uniform heat flux or excitation to the surface of the structure being analyzed using a scanning motion to scan the entire outer surface of the showerhead 10. One of the advantages of scanning a heat source with small heating area, such as a spot or line source, is providing uniform of heat fluxes to the entire showerhead 10 since the fluxes are coming from the same heat source, which improves the accuracy of the analysis.

In one embodiment, the heat source 220 may be a line source that moves in a linear motion over the structure support 230. The heat source 220 is configured to provide a substantially consistent or identical heat flux to any portion or the entire surface of the structure being analyzed, such as the showerhead 10, so that the thermal response at any portion or the entire structure can be measured and compared to adjacent areas. In one embodiment, the heat source 220 moves in a plane parallel to the plane of the supporting surface 231 or the outer surface 16 of the showerhead 10.

When analyzing the showerhead 10, the heat source 220 is configured to direct thermal energy downward to the outer surface 16 of the showerhead 10. The heat source 220 is configured to scan over the showerhead 10 disposed over the structure support 230.

The heat source 220 is coupled to an actuator 221 which moves the heat source 220 across the structure support 230 and the structure supported thereon, such as the showerhead 10. In one embodiment, the actuator 221 is a linear drive unit utilized to implement a scanning motion of the heat source 220 relative to the structure disposed on the structure support 230.

The controller 250 is connected to the heat source 220. The controller 250 is configured to switch on and off the heat source 220 at any desired frequency whereby a temperature ramp up or ramp down time at any portion or all the area that can be recorded by the camera 240 to obtain a thermal response that includes rising or falling temperature. The controller 250 is also connected to the actuator 221 to control the location of the heat source 220 to face a particular portion of the structure on the structure support 230.

The thermal response at any portion of the structure being analyzed may include different temperature or different rate of temperature change due to vertical and lateral heat conductance through the structure. As the condition of the bonding material 13 will influence the temperature profile, the thermal response is also indicative of the condition of the bonding material across the showerhead 10.

When analyzing the showerhead 10, the vertical heat conductance (heat conductance between the gas distribution plate 11 and the base 12) rather than the lateral heat conductance (heat conductance across the gas distribution plate 11 or across the base 12) is of the interest since the condition of the bonding material 13 affects mostly the vertical heat conductance. Therefore, when analyzing the showerhead 10, it is desirable that the detected thermal response is dominated by the vertical heat conductance rather than the lateral heat conductance to expose heat transfer characteristics of the bonding material 13 at the maximal degree. Vertical heat conductance dominated thermal response may be induced by controlling the combination of intensity of the heat fluxes from the heat source(s), and variation of time interval or spatial interval of heat fluxes.

In one embodiment, the dominance of the vertical heat conductance is obtained by providing a sufficiently large heat source that provides uniform or identical heat flux to any portion or entire portion of the outer surface 16 of the gas distribution plate 11. In one embodiment, the heat source 220 is a line shaped halogen lamp having a length of about equal to the diameter of the gas distribution plate 11. The dominance of the vertical heat conductance can be further enhanced by cooling the base 12 simultaneously with heating of the gas distribution plate 11 by the heat source 220. The base 12 can be cooled by using the chilled structure support 230 described above.

The camera 240 is disposed in an upper portion of the working volume 211 so that the camera 240 can capture images of the entire showerhead 10. In one embodiment, the camera 240 may be centered relative to a center of the showerhead 10 or other structure being analyzed. The camera 240 may alternatively be positioned outside the volume 211 in a position that still allows temperature sensing of the structure to be analyzed.

In one embodiment, the camera 240 operates at the infrared spectrum. In embodiment, the camera 240 operates at a spectrum including wavelength less than about 0.12 microns in wavelength from forward looking infrared (FLIR) wavelength. In another embodiment, the camera 240 operates in a spectrum includes far infrared spectrum at wavelength of several microns. In one embodiment, the camera operate at a spectrum between wavelength from less about 0.12 micron to about 30 microns.

In one embodiment, the camera 240 is an infrared camera configured to capture grayscale images that reflect temperature of the subject being photographed. The camera 240 is connected to the controller 250 which may synchronize actions between the camera 240 and the heat source 220 so that the camera 240 can take snap shots of the showerhead 10 after each heat flux from the heat source 220 to obtain thermal responses. For example, the camera 240 is configured to take a snap shot of the showerhead 10 after a fixed delay after each heat flux.

In one embodiment, the processor of the controller 250 may execute a program that operates to compile and analyze the captured images from the camera 240 and generate results indicative of the thermal profile of the showerhead 10. The results are also indicative of the condition of the bonding material 13 at the various locations of the showerhead 10.

The anti-reflective enclosure 210 is configured to shield the camera 240 from thermal noises from the environment. The anti-reflective enclosure 210 comprises light absorbing materials. In one embodiment, the anti-reflective enclosure 210 may have an inner surface 210a that is coated with an anti-reflective coating to minimize any temperature or light noises from the environment. In one embodiment, the anti-reflective coating is a black material that absorbs heat and light.

Process

Figure 5:
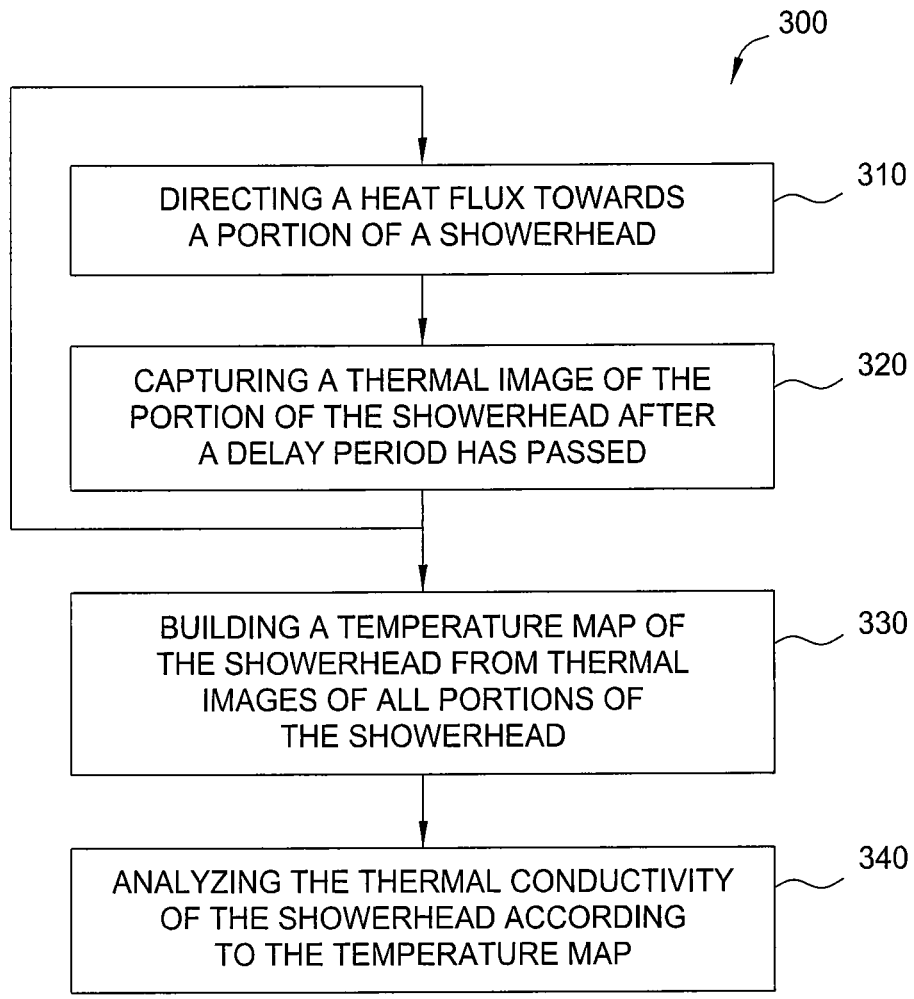
FIG. 5 is a flow diagram illustrating a method for analyzing thermal properties of a showerhead in accordance with one embodiment of the present invention.

FIG. 5 is a flow diagram illustrating a method 300 for analyzing thermal properties of the showerhead in accordance with one embodiment of the present invention. The method 300 may be performed using the thermal property analyzer 200 described above.

In box 310, a heat flux is directed to a discreet portion of the showerhead 10. When using the scanning thermal property analyzer 200, the heat source 220 may move directly above a portion of the outer surface 16 of the gas distribution plate 11 and direct a heat flux to the portion of the outer surface 16, then iteratively move above other portions of the outer surface 16 to direct a heat flux to those portions. Because the heat source 220 in one embodiment is a line lamp, the gas distribution plate 11 receives the heat flux in a band that is advanced across the outer surface 16 as the heat source 220 moves.

A heat flux may be provided in a cycle or by shuttering the heat source 220 on and off. The power supplied by the heat source 220 in a heat flux may vary in amplitude with time or be in a steady state. The heat flux may have a waveform of rectangular, saw tooth, or sinusoidal.

In box 320, a temperature information of the gas distribution plate 11 is obtained. In one embodiment, the temperature information may be in the form of a thermal image taken by the infrared camera 240. The image may include the entire gas distribution plate 11 or just the portion of the gas distribution plate 11 receiving the heat flux. In one embodiment, the thermal image may be taken after a delay period once the heat flux is turned off or moved to another area of the showerhead.

Boxes 310 and 320 may repeat with substantially uniform heat fluxes and the same delay period until the entire outer surface 16 of the gas distribution plate 11 is scanned.

In one embodiment, after the heat flux is delivered to a first portion of the gas distribution plate 11, the heat source 220 is switched off and moved to over to a second portion of the gas distribution plate 11. The thermal image of the first portion is taken after the delay period, and the next heat flux is delivered to the second portion after the effect of the previous heat flux has diminished. This process may be repeated until the entire showerhead 10 is scanned and corresponding thermal responses obtained. Portions of the showerhead 10 exhibiting higher temperature, i.e. slower thermal response, usually have less vertical thermal conductance than portions exhibiting lower temperature, i.e. faster thermal response. These differences are indicative of variation in the bonding material condition.

In another embodiment, the heat source 220 may move continuously at a constant linear speed to scan through the entire gas distribution plate 11. Continuous images or a video may be taken of the gas distribution plate 11 as the heat source 220 scans through the gas distribution plate 11 to obtain the thermal response. The portions of the showerhead having a slow thermal response are identified by a tail following the advance of the heat flux across the gas distribution plate 11 in the video images. Portions having a longer tail usually have less vertical thermal conductivity as compared to portions having shorter tail.

In box 330, a map representing thermal conductivity or thermal time constant of the showerhead 10 may be constructed from the snap shots or video images taken from the scanning process in boxes 310 and 320. The map may represent thermal conductivity in terms of temperature changes. In one embodiment, the map represents surface temperature of the entire gas distribution plate 11 taken after a fixed delay period after passage of the heat flux.

In one embodiment, the scanning process may be repeated in different direction across the showerhead 10. For example, after a first linear scan performed by the thermal property analyzer 200 to obtain a first map of surface temperature, the showerhead 10 may be rotated and boxes 310, 320, 330 repeated to obtain a second map. Analyzing the two maps in combination provides more accurate data as to the condition of the bonding material. In one embodiment, after scanning the showerhead 10 for the first time and obtaining the first map, the showerhead 10 may be rotated by 90 degrees for a second scan to obtain a second map.

In box 340, the thermal map (maps) from box 330 is used to analyze thermal properties of the showerhead 10. The thermal map may be used to identify whether the gas distribution plate 11 conducts thermal energy too fast, too slow, or not-uniform enough for producing good processing results.

In one embodiment, the obtained thermal map may be compared to a standard map to determine whether the showerhead being examined meets certain criterions. The standard map may be obtained by analyzing a showerhead that is known to be within predetermined acceptable conditions.

In another embodiment, the obtained thermal map may be compared to a stored previous map obtained from previously scanning the same showerhead 10 to determine if the thermal response of the showerhead 10 has changed over time. A change may be indicative of a loss of adherence of the bonding material 13 or other defects. This technique may be utilized to determine if the condition of the bonding material is contributing to process drift over time.

The method 300 may be performed by other apparatus with different heat sources and/or different scanning mechanisms, such as the thermal property analyzers described in FIGS. 6A-6B and 7A-7B, among others.

Embodiment with Stationary Circular Heat Source

Figure 6A:
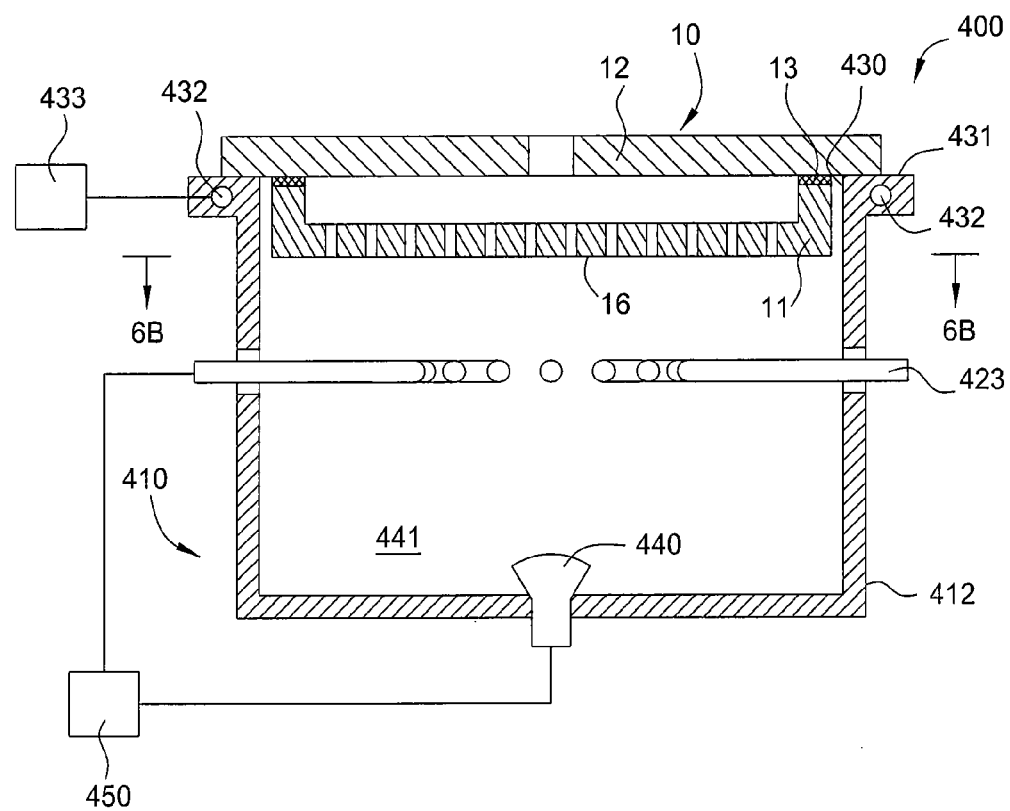
FIG. 6A is a schematic sectional side view of one embodiment of a thermal property analyzer having a stationary circular heat source.
Figure 6B:
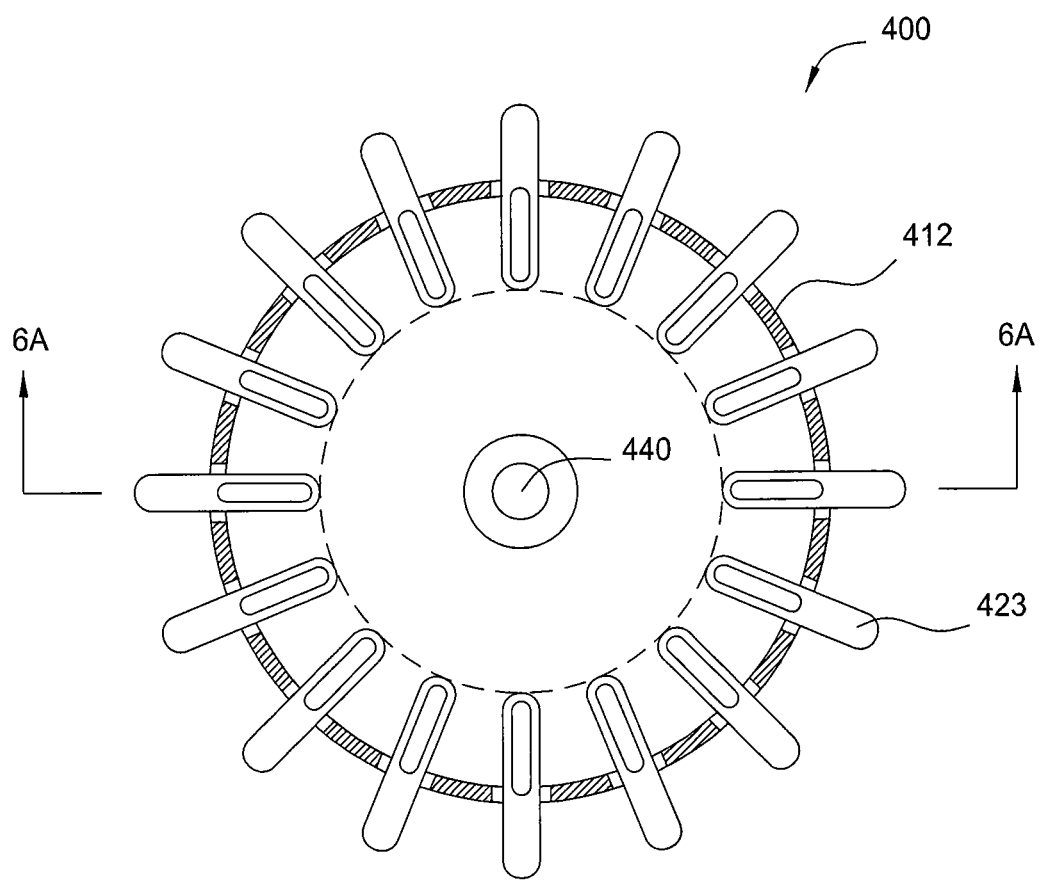
FIG. 6B is a schematic top view of the thermal property analyzer of FIG. 6A.

FIG. 6A is a schematic sectional side view of a thermal property analyzer 400 having a stationary heat source 420. The stationary heat resource 420 may be circular. FIG. 6B is a schematic top view of the thermal property analyzer 400.

The thermal property analyzer 400 includes an anti-reflective enclosure 410 defining a working volume 441. In one embodiment, the anti-reflective enclosure 410 may be cylindrical and has an upper opening 430 and a circular supporting surface 431 for receiving and supporting the showerhead 10 or other structure being analyzed. The stationary heat source 420 of the thermal property analyzer 400 is disposed in a position to provide thermal energy from the working volume 411 to the outer surface 16 of the showerhead 10. The thermal property analyzer 400 further includes a camera 440 or other temperature sensor disposed in a lower portion of the working volume 411 and configured to capture still or video images of the showerhead 10 that are indicative of the temperature of the showerhead 10. The thermal property analyzer 400 further includes a controller 450 connected to the camera 440 and the heat source 420.

In one embodiment, the thermal property analyzer 400 further includes a cooling system configured to cool the showerhead 10 being analyzed. The cooling system may comprise a cooling fluid source 433 connected to cooling channels 432 formed under the supporting surface 431.

In one embodiment, the flow rate and/or temperature of the cooling fluid are set at fixed values so that temperature of the showerhead 10 increases slightly from the heat flux during scanning/testing. In one embodiment, the temperature variations of the showerhead 10 during a scanning process are recorded and software algorithms can be applied to factor the temperature variations into the obtained thermal map for analysis.

In another embodiment, the flow rate and/or temperature of the cooling fluid are dynamically adjustable so that the showerhead 10 only incurs minimal temperature rise throughout the entire scanning/testing process. In one embodiment, the fixed temperature of the showerhead 10 dynamically maintained during scanning process becomes a parameter of the obtained thermal map for analysis.

In one embodiment, the heat source 420 comprises a plurality of heating lamps 423 evenly distributed along a sidewall 412 of the anti-reflective enclosure 410. The plurality of heating lamps 423 are configured to directing thermal energy with uniform intensity towards the showerhead 10. In one embodiment, the plurality of lamps 423 may be substantially similar, for example, being the same model, and operated in substantially similar way, such as receiving substantially the same power supply, same ramp up/ramp down time. Each of the heating lamps 423 may be turned on and off independently or in concert.

In one embodiment, the plurality of heating lamps 423 are disposed in a plane parallel to the plane of the supporting surface 431 or the outer surface 16 of the showerhead 10 supported thereon. In one embodiment, the plurality of heating lamps 423 are fixedly positioned through the sidewall 412 with a thermal emitting section inside the working volume 411 and a power connection section outside the sidewall 412. Each heating lamp 423 is connected to the controller 450, which may independently control the on and off states of the lamps. In one embodiment, the heating lamps 423 may be halogen lamps.

In one embodiment, the plurality of heating lamps 423 may run on duty cycles arranged so that substantially uniform heat fluxes are directed to different portion of the showerhead 10 in a scanning manner.

In another embodiment, the plurality of heating lamps 423 may act as a single heat source to direct a heat flux towards the entire showerhead 10 simultaneously.

The camera 440, similar to the camera 240, may be an infrared camera configured to capture grayscale images that reflect temperature of the subject being photographed. The camera 440 is connected to the controller 450 which may synchronize actions between the camera 440 and the heat source 420 so that the camera 440 can take snap shots or video images of the showerhead 10 after delivery of each heat flux from the heat source 420 to obtain thermal responses.

In one embodiment, the controller 450 may also comprise program that operates to compile the captured images from the camera 440 and generate analysis results of the showerhead 10.

During operation, the thermal property analyzer 400 may perform method 300 of FIG. 5.

In box 310, a heat flux is directed to a portion of the gas distribution plate by turning on one heating lamp 423. Unlike using the thermal property analyzer 200 when each portion receiving the heat flux is in a shape of a band, each portion receiving the heat flux has a pie shape.

In box 320, a thermal image of the gas distribution plate 11 is taken by the infrared camera 440 after a delay period once the heat flux is turned off.

Boxes 310 and 320 may be repeated until each portion of the entire gas distribution plate 11 receives substantially the same heat flux and the same delay period. In one embodiment, the scanning process may be performed by consecutively turning on and off each of the plurality heating lamps 423. In another embodiment, the scanning process may be performed by turning on and off the plurality of heating lamps 423 group by group, for example two lamps 423 are on and off at the same time, wherein the two lamps are positioned 180 degrees from one another.

In another embodiment, the heating lamps 423 may be turned on at the same time, and only one time delayed image is needed to obtain a map in box 330.

The thermal property analyzer 400 avoids motion of heat source or the showerhead, and may be efficient when more than one heating lamps can be turned on at the same time.

When all the lamps are turned on at the same time, the heat flux from the thermal property analyzer 400 may be close to the processing condition of the showerhead. Thus, the thermal property analyzer 400 may provide a thermal stress test to the showerhead 10.

Embodiment with Scanning Circular Heat Source

Figure 7A:
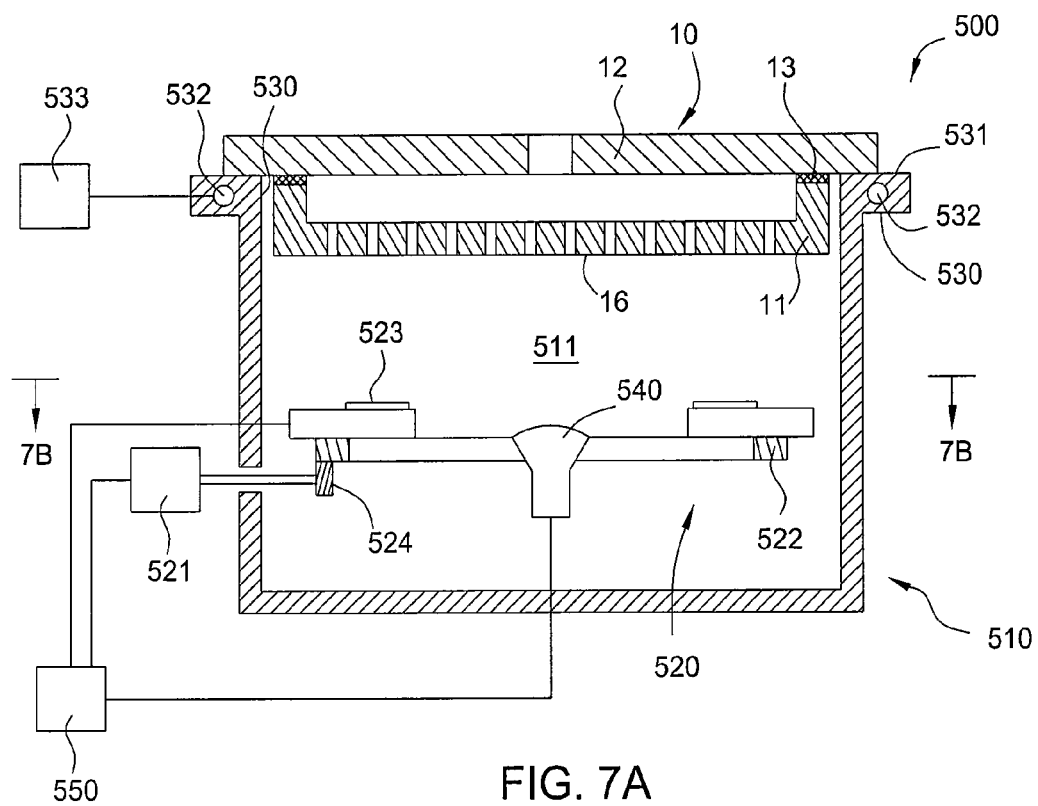
FIG. 7A is a schematic sectional side view of one embodiment of a thermal property analyzer having a scanning circular heat source.
Figure 7B:
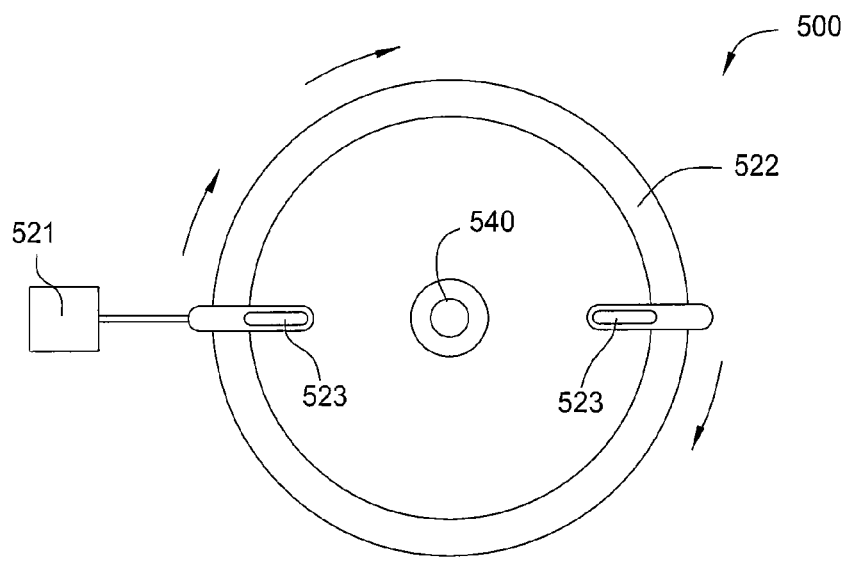
FIG. 7B is a schematic top view of the thermal property analyzer of FIG. 7A.

FIG. 7A is a schematic sectional side view of a thermal property analyzer 500 having a scanning heat source 520. The heat source 520 may be circular. FIG. 7B is a schematic top view of the thermal property analyzer 500. The thermal property analyzer 500 is similar to the thermal property analyzer 400 except the heat source 520 is movable not stationary.

The thermal property analyzer 500 has an anti-reflective enclosure 510 defining a working volume 511. In one embodiment, an anti-reflective coating may be applied to an inner surface of the anti-reflective enclosure 510 to minimize any temperature or light noises from the environment. In one embodiment, the anti-reflective coating is a black material that absorbs heat and light. In one embodiment, the anti-reflective enclosure 510 may be cylindrical and has an upper opening 530 and a circular supporting surface 531 for receiving and supporting the showerhead 10 or other structure being analyzed. The scanning heat source 520 is disposed in the working volume 511 for directing thermal energy towards the outer surface 16 of the showerhead 10. The thermal property analyzer 500 further comprises a camera 540 disposed in a lower portion of the working volume 511 and configured to capture still or video images of the showerhead 10. The thermal property analyzer 500 further comprises a controller 550 connected to the camera 540 and the heat source 520.

In one embodiment, the thermal property analyzer 500 further comprises a cooling system configured to cool the showerhead 10 being analyzed. The cooling system may comprise a cooling fluid source 533 connected to cooling channels 532 formed under the supporting surface 531.

In one embodiment, the scanning heat source 520 comprises two heating lamps 523 coupled to a circular frame 522 positioned substantially concentric with the showerhead 10. The circular frame 522 has gears that are engaged with a gear 524 driven by a motor 521. The motor 521 rotates the circular frame 522 via the gear 524 so that the lamps 523 rotate about a center of the circular frame 522 and rotate into alignment with various portions of the showerhead 10. One or more heating lamps 523 may be present for scanning the showerhead 10 during operation. In one embodiment, the two heating lamps 523 are positioned at 180 degrees from one another.

Similar to the heating lamps 423, the heating lamps 523 may be on constantly or intermittently to direct discrete heat fluxes while scanning the showerhead 10 during operation. In one embodiment, the heat lamps 523 move in a plane parallel to the plane of the supporting surface 531 or the outer surface 16 of the showerhead 10 supported thereon.

The thermal property analyzer 500 may perform method 300 of FIG. 5 in a manner similar to the thermal property analyzer 400. In box 310, a heat flux is directed to a portion of the gas distribution plate by turning on and rotating the heating lamp 523.

In box 320, a thermal video of the gas distribution plate 11 is taken by the infrared camera 540. A heat tail following the portion of the showerhead 10 receiving the heat flux in the thermal video reflects thermal properties of the showerhead 10.

The thermal property analyzer 500 reduces the number of lamps used during operation making the analyzing results less dependent on the uniformity of the lamps.

ADVANTAGES AND APPLICATION

Embodiments of present invention provide non-contacting method for effectively monitoring thermal property of a showerhead or other structures.

Embodiments of the present invention may be used in quality control for manufacturer of a composite structure, such a showerhead, to ensure uniform thermal properties of the composite structure. A showerhead manufacturer may use embodiments of the present invention to determine whether a showerhead's thermal properties are fit for processing.

Embodiments of the present invention can also be used for maintaining a composite structure, such as a showerhead, and monitoring the lifetime of the composite structure. For example, a showerhead including two or more pieces glued together by bonding materials can be routinely analyzed using embodiments of the present invention to make sure that otherwise hard to inspect bonding materials are still fit for production and/or are contributing to process drift.

Embodiments of the present invention can also be used for various analysis purposes. For example, in semiconductor manufacturing, embodiments of the present invention may be used to obtain thermal properties of a showerhead to diagnose whether certain defects of the chamber, such as non-uniformity, is caused by the non-uniform thermal conductivity of the showerhead.

Even though a showerhead having multiple components are described with embodiments of the present invention, persons skilled in art would recognize that embodiments of the present invention may be used in analyzing thermal properties of any structure.

While the foregoing is directed to embodiments of the present invention, other and further embodiments of the invention may be devised without departing from the basic scope thereof, and the scope thereof is determined by the claims that follow.

What is claimed is:

1. An apparatus for analyzing thermal property of a structure comprising a first component, a second component, and a bonding material joining the first component to the second component, comprising:
    a structure support having a supporting surface configured to support the structure by contacting the second component, wherein the structure support has cooling channels for circulating a cooling fluid to accelerate dissipation of thermal energy from the structure supported by the substrate support;
    a heat source comprising one or more heating elements, wherein when the structure is supported by the supporting surface of the structure support, the first component faces the heat source and the second component faces away from the heat source, and the heat source directs a heat flux to a surface of the first component; and
    a camera facing the structure supported on the structure support and configured to capture thermal images of the structure supported on the structure support.

2. The apparatus of claim 1, further comprising an enclosure defining a working volume, wherein the enclosure comprises an anti-reflective coating coated on an inner surface of the enclosure, and the camera, the heat source and the first surface of the structure are disposed in the working volume.

3. The apparatus of claim 1, wherein the one or more heating elements are movable in a plane parallel to a plane of the structure support.

4. The apparatus of claim 3, wherein the heat source comprises:
    a line heating lamp parallel to the supporting surface; and
    a linear drive unit coupled to the line heating lamp.

5. The apparatus of claim 3, wherein the heat source comprises:
    a circular frame disposed concentric to the structure support;
    a driving mechanism configured to rotate the circular frame about a center of the circular frame; and
    two heating lamps coupled to the circular frame.

6. The apparatus of claim 1, wherein the heat source comprises a plurality of heating lamps evenly distributed above the structure support.

7. The apparatus of claim 1, wherein the cooling channels cool an edge region of the structure.

8. The apparatus of claim 1, wherein the camera is an infrared camera.

9. An apparatus for analyzing thermal property of a showerhead comprising a gas distribution plate, a base, and a bonding material joining the gas distribution plate and the base, comprising:
    an anti-reflective enclosure defining a working volume;
    a heat source comprising one or more heating elements disposed in the working volume;
    a structure support having a supporting surface configured to contact the base of the showerhead so that the gas distribution plate faces the heat source and the base faces away from the heat source, wherein the heat source is positioned to direct a heat flux to the gas distribution plate of the showerhead supported by the structure support, and the structure support has cooling channels for circulating a cooling fluid to accelerate dissipation of thermal energy from the base of the showerhead; and
    a camera disposed in the working volume facing the structure support and configured to capture thermal images of the gas distribution plate.

10. The apparatus of claim 9, wherein the heat source comprises:
    an actuator configured to move the one or more heating elements in a plane parallel to a plane of the support structure.

11. The apparatus of claim 10, wherein the one or more heating elements comprise a line heating lamp, and the actuator is a linear drive unit configured to move the line heating lamp linearly.

12. The apparatus of claim 9, wherein the heat source comprises a plurality of stationary heating lamps evenly distributed above the supporting structure.

13. A method for analyzing condition of a composite structure comprising a first component, a second component, and a bonding material joining the first component and the second component, comprising:
    positioning the composite structure on a structure support so that the second component contacts the structure support, the first component faces a heat source, and the second component faces away from the heat source;
    directing a heat flux from the heat source towards the first component while cooling the second component by following a cooling fluid in cooling channels in the structure support;
    capturing a thermal image of the first component after the heat flux;
    building a temperature map of the first component from the captured thermal image; and
    determining condition of the bonding material according to the temperature map.

14. The method of claim 13, wherein directing a heat flux comprises consecutively directing substantially uniform heat fluxes towards portions of the first component in a scanning manner.

15. The method of claim 14, wherein directing uniform heat fluxes towards portions of the first component comprises moving the heat source relatively to and parallel with the first component to scan the first component.

16. The method of claim 15, wherein moving the heat source comprises moving a line heating lamp linearly relative to the first component or rotating one or more heating lamps about a central axis of the first component.

17. The method of claim 14, wherein capturing the thermal image comprises capturing a thermal image after a delay period for each heat flux, building a temperature map comprises compiling the thermal images taken after the heat fluxes.

* * * * *